United States Patent [19]

Johnson et al.

[11] Patent Number: 4,463,175
[45] Date of Patent: * Jul. 31, 1984

[54] MOLYBDENUM TRIOXIDE LAYERED COMPOUNDS

[75] Inventors: Jack W. Johnson, Fanwood; Allan J. Jacobson, Princeton, both of N.J.

[73] Assignee: Exxon Research & Engineering Co., Florham Park, N.J.

[*] Notice: The portion of the term of this patent subsequent to Oct. 19, 1999 has been disclaimed.

[21] Appl. No.: 403,057

[22] Filed: Jul. 29, 1982

Related U.S. Application Data

[63] Continuation-in-part of Ser. No. 205,142, Nov. 10, 1980, Pat. No. 4,355,161.

[51] Int. Cl.$^3$ .............................................. C07F 11/00
[52] U.S. Cl. .......................................... 544/225; 546/2
[58] Field of Search ............................ 546/2; 544/225

[56] References Cited

U.S. PATENT DOCUMENTS

| | | | |
|---|---|---|---|
| 3,489,775 | 1/1970 | Seree de Roch et al. | 260/348.5 |
| 3,688,109 | 8/1972 | Gamble | 250/51.5 |
| 3,766,064 | 10/1973 | Gamble et al. | 252/25 |
| 4,009,122 | 2/1977 | Lines et al. | 252/431 N |
| 4,010,217 | 3/1977 | Zuech | 260/283 |
| 4,049,887 | 9/1977 | Whittingham | 429/112 |
| 4,094,893 | 6/1978 | Dines | 260/429 R |
| 4,153,792 | 5/1979 | Kroenke | 544/181 |
| 4,355,162 | 10/1982 | Johnson | 546/2 |

FOREIGN PATENT DOCUMENTS

1377213  5/1972  United Kingdom .

OTHER PUBLICATIONS

J. Bernard et al., C. R. Acad. Sci., Paris, Ser. C, vol. 263, pp. 1068–1071, 1966.
M. Camelot, Revue de Chimie Minerale, vol. 6, pp. 853–883, 1969.
Yamamoto et al., Chem. Abstr., vol. 87, 135055p, 1977.
Gol'dberg et al., Chem. Abstr., vol. 89, 43124g (1978).
Jovel et al., Chem. Abstr., vol. 87, 183719e (1977) and vol. 85, 123034b (1976).
Jurels et al., Chem. Abstr., vol. 82, 155, 165z and 155, 166a (1974).
Sonnemans et al., Chem. Abstr., vol. 81, 3017u (1972).
Arakawa et al., Chem. Abstr., vol. 84, 58282u (1976).

*Primary Examiner*—Mark L. Berch
*Attorney, Agent, or Firm*—James H. Takemoto; Jay Simon

[57] ABSTRACT

A new composition of matter comprising molybdenum trioxide and heterocyclic nitrogen or oxygen Lewis bases. The molybdenum trioxide, upon reaction with Lewis base, forms a layered compound characterized in that the Lewis base is covalently bonded to molybdenum atoms in molybdenum oxide layers. The layered compound has the formula $LMoO_3$ or $L_{\frac{1}{2}}MoO_3$ where L is a Lewis base containing nitrogen or oxygen electron donors and selected from the group consisting of 5- and 6-membered heterocyclic amines, amine oxides, triorganophosphates, phosphine oxides and sulfoxides. L has the steric requirement such that its maximum cross-sectional area perpendicular to an axis running through the L-Mo covalent bond is less than about 30(Å)$^2$.

4 Claims, 4 Drawing Figures

MOLYBDENUM TRIOXIDE LAYERED COMPOUNDS

CROSS-REFERENCE TO RELATED APPLICATIONS

This application is a Continuation-in-Part of Application Ser. No. 205,142 filed Nov. 10, 1980, now U.S. Pat. No. 4,335,161.

BACKGROUND OF THE INVENTION

This invention relates to unique layered compounds formed by reacting molybdenum trioxide with a Lewis base. More particularly, Lewis bases are covalently bound to molybdenum atoms within a layered molybdenum oxide structure.

Transition metal complexes of molybdenum are well-known, e.g., $[Mo(NCS)_6]^{3-}$ and $[Mo(2,2'\text{-bipyridine})_3]^{3+}$. U.S. Pat. Nos. 3,489,775 and 4,153,792 describe molybdate salts formed from the reaction of molybdic acid, $MoO_3$ or molybdenum salts with organic nitrogenous bases. U.S. Pat. No. 4,009,122 teaches a molybdenum catalyst which is the reaction product of an oxygen containing molybdenum compound, an amine and an alkylene glycol. U.S. Pat. No. 4,010,217 relates to coordination complexes of molybdenum or tungsten with nitric oxide.

It is also known that molybdenum dichalcogenides can form intercalation compounds. Intercalation compounds wherein an organic isonitrile is intercalated into the layered structure of Group IVb, Vb, molybdenum and tungsten transition metal dichalcogenides where the chalcogenide is sulfur, selenium or tellurium, are taught in U.S. Pat. No. 4,094,893. The general properties and methods of preparation of intercalation compounds are described in U.S. Pat. Nos. 3,766,064 and 3,688,109. As set forth therein, the intercalate occupies vacant sites between the layers of the metal chalcogenide wherein the chalcogenide is sulfur, selenium or tellurium. The intercalated species include organic and inorganic compounds which are broadly electron donors, electron acceptors, have substantial polarization interactions or are capable of d-orbital bonding. U.S. Pat. No. 4,049,887 relates to an improved cathode containing as active material a layered compound of the formula $MA_xB_y$ where M is Fe, V, Ti, Cr or In, A is O, S, Se or Te, and B is Cl, Br or I.

J. Bernard and M. Camelot, C. R. Acad. Sci., Paris, Ser. C, 263:1068 (1966) report on the reaction of molybdenum trioxide, molybdenyl chloride and molybdenum dioxydichloride with pyridine. The products were identified as addition compounds of the formulae: $C_5H_5N.MoO_3$, $(C_5H_5N)_4.MoO_3.2HCl$ and $(C_5H_5N)_2.MoO_2Cl_2$. The authors noted that $C_5H_5N.MoO_3$ could only be prepared in sealed ampoules at high temperatures. In a subsequent work, M. Camelot, Revue de Chimie Minerale, 6, 853 (1969), studied addition compounds of pyridine with some oxychlorides or trioxides of chromium, molybdenum and uranium. Based on an infrared spectroscopic investigation, Camelot concluded that $C_5H_5N.MoO_3$ was a molecular coordination compound.

The preparative method described by Camelot or Bernard and Camelot for $MoO_3.C_5H_5N$ is similar to a preparative technique for heavy metal chalcogenides intercalated with organic nitrogen compounds described in U.S. Pat. Nos. 3,766,064 or 3,688,109. Molybdenum, however, is not listed as a metal capable of forming a heavy metal layered chalocogenide with, e.g., pyridine. As noted above, Camelot concluded, based on his observations, that $MoO_3.C_5H_5N$ was simply another molecular coordination compound similar to $CrO_3.C_5H_5N$ and $C_5H_5N.SO_3$.

SUMMARY OF THE INVENTION

It has been discovered that molybdenum trioxide and Lewis bases can form new compounds having a unique layered structure. The present composition of matter comprises layered compounds of the formula $LMoO_3$ where L is a Lewis base containing nitrogen or oxygen electron donors and selected from the group consisting of 5-membered heterocyclic amines, 6-membered heterocyclic amines, amine oxides, triorganophosphates, phosphine oxides and sulfoxides with the proviso that the nitrogen donor cannot be substituted pyridine, the layered compounds being characterized in that L is covalently bound to a molybdenum atom in the molybdenum oxide layer and L has the stearic requirement such that the maximum cross-sectional area of L perpendicular to an axis running through the L-Mo covalent bond is less than about 30 (Å)$^2$.

In compounds of the invention, a neutral Lewis base is coordinated to a molybdenum atom in the manner of a molecular coordination complex. In contrast to the description by Camelot in Revue de Chimie Minerale, 6, 853 (1969) for $C_5H_5N.MoO_3$, however, the present compounds are not molecular coordination complexes such as $MoO_2Cl_2.2C_5H_5N$ or $(\text{dien})MoO_3$ wherein dien is diethylenetriamine (Inorg. Chem., 3, 397 (1964)) because the present compounds have an infinitely connected 2-dimensional or 3-dimensional layered structure. Moreover, the present compounds possessing a layered structure are distinguished from intercalation compounds in that their layered structure is distinct from the layered structure of the starting $MoO_3$.

DETAILED DESCRIPTION OF THE INVENTION

Figure 1:
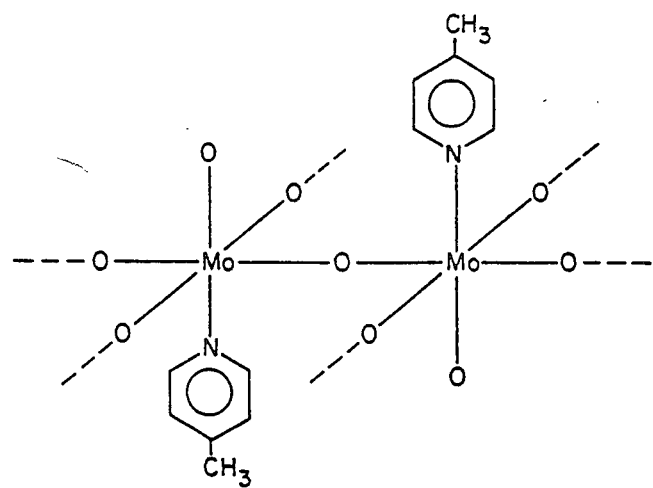
FIG. 1 is a schematic diagram of the bonding arrangement of (4-methylpyridine)$MoO_3$.

Lewis bases which form the layered compounds of the invention are those which have heterocyclic nitrogen donors and oxygen donors, preferably 5- and 6-membered heterocyclic amine donors and especially 6-membered heterocyclic amine donors. Preferred nitrogen donors are substituted pyridines having the formula

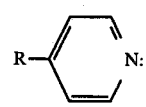

where R is halogen; $C_1$–$C_{20}$, preferably $C_1$–$C_{10}$ aliphatic; $C_6$–$C_{10}$ aryl, preferably phenyl which may be substituted in the 4-position by halogen or $C_1$–$C_6$ alkyl;

$C_7$-$C_{20}$ aralkyl; OR' or SR' where R' is $C_1$-$C_6$ alkyl. Examples are

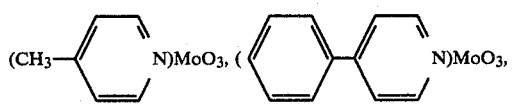

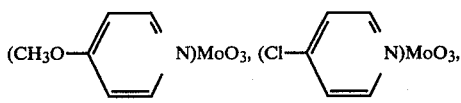

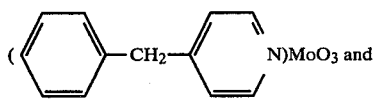

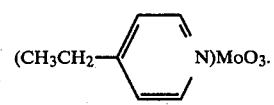

Other 5- and 6-membered heterocyclic amines which may form layered compounds include pyridazine, pyrimidine, pyrazine, triazine, N-substituted oxazine, N-substituted imidazole, oxazole and thiazole.

A Lewis base which is a bidentate heterocylic nitrogen ligand forms compounds of the formula $L_\frac{1}{2}MoO_3$, preferably compounds of the formulae

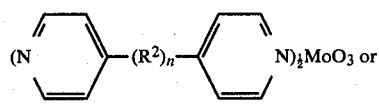

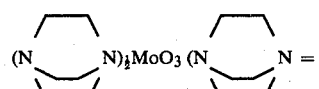

1,4-diaza[2.2.2]bicyclooctane) where n is 0 or 1 and $R^2$ is methylene, alkylene, alkenylene or alkynylene of 2-6 carbon atoms; $C_6$-$C_{10}$ arylene, preferably paraphenylene; $C_7$-$C_{14}$ aralkylene, preferably

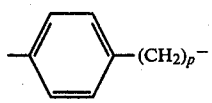

where p is from 1-6; oxygen or sulfur. The bidentate ligands form connecting linkages between separate molybdenum oxide layers.

Oxygen donors may be amine oxides, triorganophosphates, phosphine oxides or sulfoxides.

Unlike the heavy metal chalcogenides employed in intercalation compounds such as those reported in U.S. Pat. No. 3,766,064, molybdenum trioxide may be used in the present invention without any special pretreatment other than drying. Thus, commercially available dried molybdenum trioxide is heated with an appropriate Lewis base in a sealed tube at temperatures of from 100° to 400° C., preferably 150° to 250° C. for up to 60 days, preferably from about 1-25 days. The amount of Lewis base is not critical and a stoichiometric amount or an excess may be used. It is preferred to evacuate the tube prior to sealing to minimize the possibility of oxidation of Lewis bases at elevated temperature. The rate of reaction may be accelerated if the Lewis base and $MoO_3$ are preground in a micronizing mill. An inert organic solvent may be present if desired. At higher temperatures such as 250° C., it is possible that the metal oxide itself can lead to oxidation of Lewis base. It is also preferred to use substantially anhydrous Lewis bases. Alternatively, layered compounds may be prepared by contacting an ionic molybdate salt with the protonated Lewis base as cation in the presence of Lewis base and molecular sieves. A reaction is shown as follows:

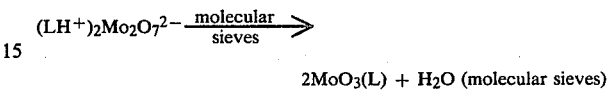

$2MoO_3(L) + H_2O$ (molecular sieves)

Water produced by the reaction is taken up by the molecular sieves.

The preparation of a compound pyridine.$MoO_3$ has been reported (C. R. Acad. Sci., Paris, Ser. C, 263:1068 (1966)). This compound was later studied in detail (Revue de Chimie Minerale, 6, 853 (1969)). The latter spectroscopic study investigated the spectrum of both uncoordinated and coordinated pyridine as well as changes in skeletal vibrations of the inorganic part of the compound. The author reported that $CrO_3$, $2C_5H_5N$; $CrO_3$, $C_5H_5N$; $MoO_3$, $C_5H_5N$; $UO_3$, $C_5H_5N$; $MoO_2Cl_2$, $2C_5H_5N$; $UO_2Cl_2$, $4C_5H_5N$ and $U_2O_5Cl_2,3C_5H_5N$ all possess the characteristic bands of pyridine coordination compounds. It is probable, however, that the characterization of $C_5H_5N$, $MoO_3$ as a typical coordination complex is not accurate.

The layered compounds of the present invention do possess the covalent bonding characteristic of molecular coordination compounds. They are not, however, molecular coordination compounds since they possess 2-dimensional or 3-dimensional extended lattices. In the case of 2-dimensional extended lattices, the parallel layers of neutral $LMoO_3$ are held together by relatively weak forces, i.e., van der Waals forces with interlayer spacing depending on the size of the Lewis base. A 3-dimensional extended lattice results when a bidentate Lewis base such as 4,4'-bipyridine is inserted between the parallel layers. The interlayer spacing is increased and separate parallel layers are bound together by covalent bonding between each layer and the functional moieties of the bidentate Lewis base. While 2- and 3-dimensional extended lattices are layered compounds, they are not intercalation compounds such as are reported in U.S. Pat. No. 3,766,064. The latter compounds are generally the result of electrostatic interactions wherein the nitrogen atom of the intercalated guest is equidistant between the layers of the intercalation host and the arrangement of host atoms within the lattice is essentially unchanged.

Rather, the instant layered compounds possess a unique physical structure as shown in FIG. 1 which is a schematic diagram of the bonding arrangement in

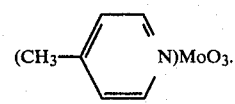

Figure 2:
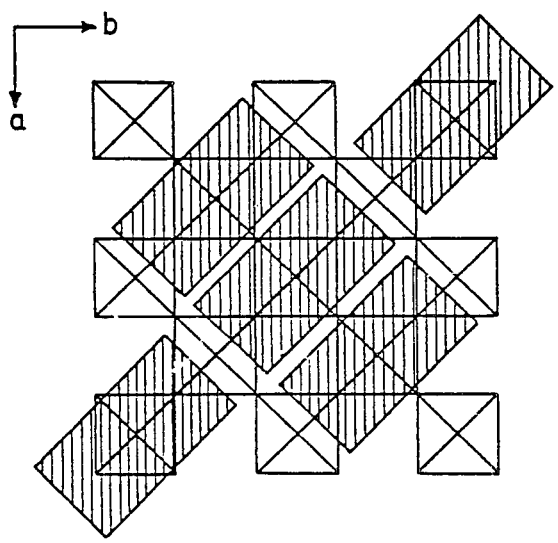
FIG. 2 is a schematic diagram of the 001 projection of (4-methylpyridine)$MoO_2$ showing the van der Waals packing of the 4-methylpyridine molecules.
Figure 3:
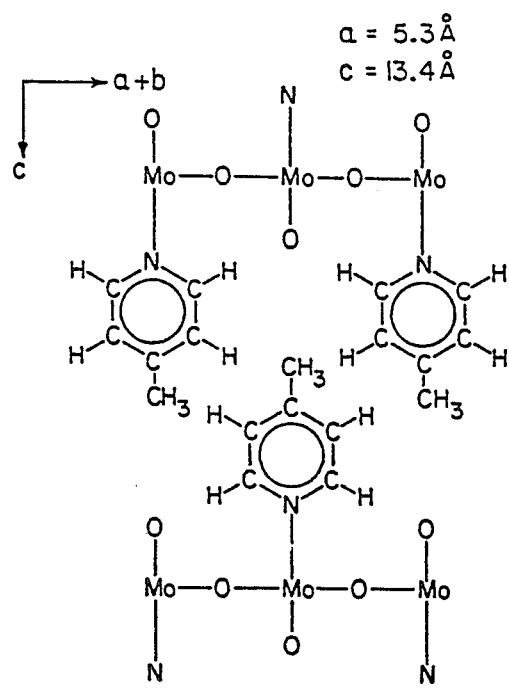
FIG. 3 is a schematic diagram of the 110 projection of the structure of (4-methylpyridine)$MoO_3$.

As illustrated in this figure, 4-methyl pyridine occupies space between the molybdenum oxide layers and bonds directly to a Mo atom. The overall layered structure is shown in FIGS. 2 and 3 which depict the 001 projection of the structure of

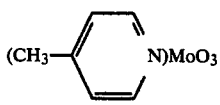

showing van der Waals packing of the

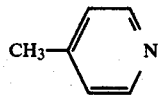

molecules as designated by the cross-hatching and the 110 projection of

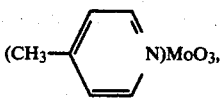

respectively. The nature of L determines the separation of MoO$_3$ layers, e.g., (pyridine)MoO$_3$ has an interlayer separation of 11.5 Å, (4-methylpyridine).MoO$_3$ a separation of about 13.4 Å, and (4-phenylpyridine).MoO$_3$ a separation of about 20.4 Å. As can be seen from the figures, the layers are composed of MoO$_5$L octahedra sharing corner oxygen atoms. The Lewis base is trans to the single unshared oxygen. Based on x-ray studies, it can be determined that in order for the Lewis base to bond to Mo atoms, it must meet the steric requirement such that the maximum cross-sectional area of the Lewis base perpendicular to an axis running through the Lewis base-Mo covalent bond is less than about 30 (Å)$^2$. Thus bulky Lewis bases such as triethylamine or triphenylphosphine will not form layered compounds according to the invention because of the above-mentioned structural considerations.

Figure 4:
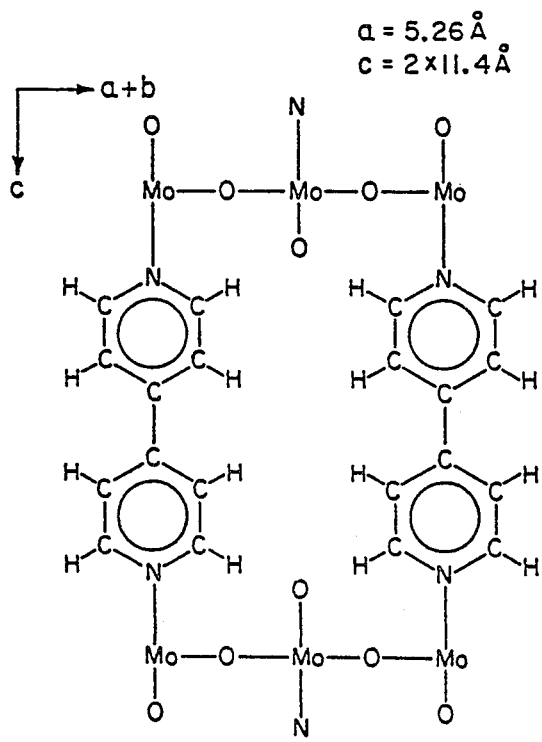
FIG. 4 is a schematic diagram of the bonding arrangement of (4,4'-bipyridine)$_{\frac{1}{2}}MoO_3$.

When a bidentate Lewis base is incorporated into the LMoO$_3$ structure, separate molybdenum oxide layers can be bound together. For example, when 4,4'-bipyridine is employed, each separate pyridine ring can bind to molybdenum atoms in adjacent molybdenum oxide layers thus forming a composition wherein individual layers within the overall LMoO$_3$ crystal structure are bound together by bridging 4,4'-bipyridine molecules. This is shown schematically in FIG. 4. These bridged layered compounds are unique in that they exhibit a higher degree of thermal stability than the corresponding unbridged compounds.

If the x-ray powder pattern analysis of the layered reaction products shows lines characteristic of the MoO$_3$ starting material, regrinding and continued reaction can lead to a pure LMoO$_3$ product. The x-ray analysis further demonstrates that the interlayer distance correlates with the size of specific Lewis bases between the layers. Thermogravimetric analysis indicates the loss of Lewis base corresponding to a 1:1 or 2:1 MoO$_3$:L composition. The 2:1 ratio reflects a bridging ligand such as 4,4'-bipyridine.

The layered compounds of the invention possess unique properties. First, they have a 2-dimensionally or 3-dimensionally bonded layered structure with molybdenum in its highest oxidation state. Moreover, the present products are generally pale green and have higher thermal stability as compared to the dark blue pyridinium molybdenum bronzes reported by Schollhorn et al., Mat. Res. Bull., 11, 83 (1976). The instant 2- and 3-dimensionally bonded layered compounds are useful in electrochromic devices and as cathode materials in electrochemical cells, e.g., lithium batteries as described in U.S. Pat. No. 4,049,887.

The following examples are further illustrative of the invention.

EXAMPLE 1

The preparation of

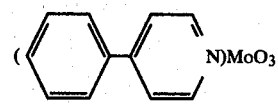

is illustrated as follows. A pyrex tube containing MoO$_3$ and excess solid 4-phenylpyridine was evacuated, sealed and heated for eight days at 170° C. After cooling, the tube was opened and the contents isolated. Solid 4-phenylpyridine was removed from the product by washing with toluene. The sample was reground and resealed in pyrex with 4-phenylpyridine and reheated for a further ten days. The product was isolated as described above and characterized by x-ray powder diffraction and thermogravimetric analysis. The x-ray powder data showed a well defined 001 series of lines corresponding to an interlayer separation of 20.4 Å. A small amount of unreacted MoO$_3$ was also detected. Thermogravimetric analysis gave an observed weight loss of 47.7% compared to a theoretical weight loss of 51.9% based on a 1:1 stoichiometry.

EXAMPLE 2

The general procedure of Example 1 was repeated except that 4-methylpyridine was substituted for 4-phenylpyridine. After heating for 15 days at 175° C. a dark colored product was isolated. The x-ray powder pattern showed a well-developed 001 series of lines corresponding to the formation of (4-methylpyridine)-MoO$_3$ with an interlayer separation of 13.4 Å. Unreacted MoO$_3$ was also detected in the powder pattern.

EXAMPLE 3

The procedure of Example 1 was repeated but in this case a solution of 4,4'-bipyridine in xylene was used and the MoO$_3$ was preground in a micronizing mill. A mixture of preground MoO$_3$ was heated with an excess of the 4,4'-bipyridine/xylene solution for four days at 250° C. After isolation and regrinding the reaction mixture was reheated for four days at 250° C. Finally the product was isolated, micronized and reheated in the 4,4'-bipyridine/xylene solution for five days at 250° C. Thermogravimetric analysis showed a weight loss of 35.2% which leads to the formulation

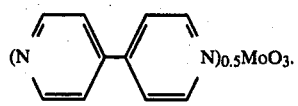

The x-ray powder diffraction pattern showed no lines for MoO$_3$ and a well-developed 001 series corresponding to a layer spacing of 11.4 Å. Well-developed mixed (hkl) diffraction lines were also observed and the entire pattern could be indexed using a body-centered tetragonal unit cell with lattice parameters a=5.26 Å and c=22.8 Å. The doubled c axis and the stoichiometry demonstrate that the 4,4'-bipyridine ligands crosslink the molybdenum oxygen layers.

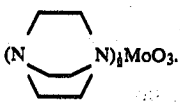

What is claimed is:

1. A composition of matter comprising layered compounds containing MoO₃ and a nitrogen donor Lewis base, said layered compounds having the formulae

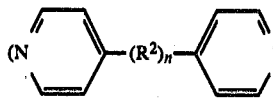 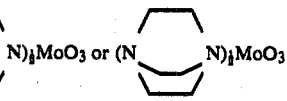

where n is 0 or 1 and R² is methylene, alkylene, alkenylene or alkynylene of 2 to 6 carbon atoms, C₆-C₁₀ arylene, C₇-C₁₄ aralkylene, oxygen or sulfur, the layered compounds being characterized in that the nitrogen donor Lewis base is covalently bound to molybdenum atoms in separate molybdenum oxide layers and the Lewis base has the steric requirement such that the maximum cross-sectional area of said base perpendicular to an axis running through the Lewis base-Mo bond is less than about 30 (Å)².

2. The composition of claim 1 wherein R² is methylene, alkylene of 2-6 carbon atoms, paraphenylene,

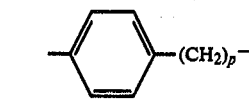

where p is from 1 to 6, O or S.

3. The composition of claim 1 wherein the layered compound is

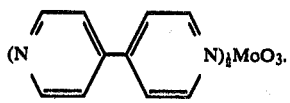

4. The composition of claim 1 wherein the layered compound is